(12) United States Patent
Barth et al.

(10) Patent No.: US 6,916,838 B1
(45) Date of Patent: Jul. 12, 2005

(54) 1-BENZYLPYRAZOLE-3-CARBOXYLIC ACID TRICYCLIC DERIVATIVES AS CANNABINOID RECEPTOR ANTAGONISTS

(75) Inventors: Francis Barth, Saint-Georges-d'Orques (FR); Joseph Millan, Juvignac (FR); Didier Oustric, Le Cres (FR); Murielle Rinaldi, Saint-Georges-d'Orques (FR); Martine Vernhet, Montpellier (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/111,916

(22) PCT Filed: Nov. 2, 2000

(86) PCT No.: PCT/FR00/03047

§ 371 (c)(1),
(2), (4) Date: Jul. 31, 2002

(87) PCT Pub. No.: WO01/32629

PCT Pub. Date: May 10, 2001

(30) Foreign Application Priority Data

Nov. 3, 1999 (FR) .............................................. 99 13847

(51) Int. Cl.⁷ ..................... A61K 31/416; C07D 231/54
(52) U.S. Cl. .................. 514/406; 548/356.1; 548/359.1
(58) Field of Search ........................... 548/359.1, 356.1; 514/406

(56) References Cited

U.S. PATENT DOCUMENTS

| 5,624,941 A | 4/1997 | Barth et al. |
| 5,696,143 A | 12/1997 | Talley et al. |
| 5,925,768 A | 7/1999 | Barth et al. |
| 5,948,777 A | * 9/1999 | Bender et al. ............ 514/235.8 |
| 5,990,170 A | * 11/1999 | Della Valle et al. ......... 514/613 |

FOREIGN PATENT DOCUMENTS

| EP | 0656354 | 6/1995 |
| GB | 1382773 | 2/1975 |
| WO | WO 96/09304 | 3/1996 |

* cited by examiner

*Primary Examiner*—Golam M M Shameem
(74) *Attorney, Agent, or Firm*—Michael D. Alexander; Kelly L. Bender; Paul R. Darkes

(57) ABSTRACT

Tricyclic derivatives of 1-benzylpyrazole-3-carboxylic acid which are antagonists of the cannabinoid $CB_2$ receptors; their method of preparation and pharmaceutical compositions containing them.

14 Claims, No Drawings

1-BENZYLPYRAZOLE-3-CARBOXYLIC ACID TRICYCLIC DERIVATIVES AS CANNABINOID RECEPTOR ANTAGONISTS

CROSS-REFERENCE TO RELATED APPLICATION

This application is a 35 U.S.C. §371 application of PCT International Application No. PCT/FR00/03047 filed Nov. 2, 2000, which in turn claims priority from French Application No. 99/13847, filed Nov. 3, 1999.

The subject of the present invention is compounds which are antagonists of the cannabinoid $CB_2$ receptors, their preparation, pharmaceutical compositions containing them. The compounds of the invention are tricyclic derivatives of 1-benzylpyrazole-3-carboxylic acid.

Patent applications EP-A-576 357, EP-A-658 546 and WO-97/19063 describe pyrazole derivatives having affinity for the cannabinoid receptors. More particularly, patent application EP-A-656 354 claims N-piperidino-5-(4-chlorophenyl)-1-(2,4-dichlorophenyl)-4-methylpyrazole-3-carboxamide and its pharmaceutically acceptable salts which have a very good affinity for the cannabinoid $CB_1$ receptors. Patent application EP-A-868 420 describes pyrazole-3-carboxamide derivatives substituted at the 1-position of pyrazole by a variously substituted benzyl group.

International patent application WO-96/09304 describes compounds inhibiting cyclooxygenase, more specifically cyclooxygenase-2. These compounds, which are useful in the treatment of inflammation and inflammatory diseases, correspond to the formula:

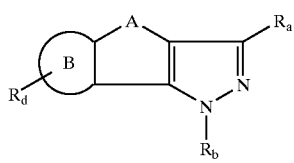

in which:

A, B, $R_a$, $R_b$, $R_d$ have different meanings.

Novel tricyclic derivatives of 1-benzylpyrazole-3-carboxylic acid have now been found which possess a very good affinity for the cannabinoid $CB_2$ receptors and which are useful in the therapeutic fields where *cannabis* is known to be involved.

$\Delta^9$-THC is the main active constituent extracted from *Cannabis sativa* (Tuner, 1985; In Marijuana 84, Ed. Harvey, D Y, IRL Press, Oxford).

The effects of the cannabinoids are due to an interaction with specific receptors of high affinity which are present at the central level (Devane et al., Mol. Pharmacol., 1988, 34, 605–613) and peripheral level (Nye et al., Pharmacol. and Experimental Ther., 1985, 234, 784–791; Kaminski et al., 1992, Mol. Pharmacol., 42, 736–742; Munro et al., Nature, 1993, 365, 61–65).

The characterization of the receptors has been made possible by the development of synthetic ligands for the cannabinoid receptors such as the agonists WIN 55212-2 (J. Pharmacol. Exp. Ther., 1993, 264, 1352–1363) or CP 55,940 (J. Pharmacol. Exp. Ther., 1988, 247, 1046–1051).

The subject of the present invention is compounds of formula:

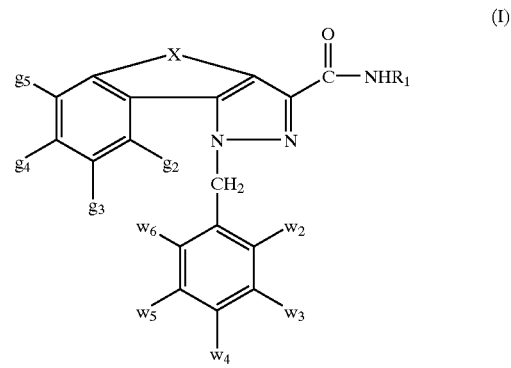

in which:

X— represents a group —$(CH_2)_n$—;

n is equal to 1 or 2;

$g_2$, $g_3$, $g_4$, $g_5$, $w_2$, $w_3$, $w_4$, $w_5$, $w_6$ are identical or different and each independently represent hydrogen, a halogen, a trifluoromethyl, a ($C_1$–$C_4$)alkyl, a ($C_1$–$C_4$)alkoxy, a ($C_1$–$C_4$)alkylthio, a nitro;

$R_1$ represents a nonaromatic $C_3$–$C_{15}$ carbocyclic radical which is unsubstituted or substituted one or several times with a ($C_1$–$C_4$)alkyl;

as well as their salts and their solvates.

The expression alkyl is understood to mean straight or branched alkyls. The methyl, ethyl, propyl, isopropyl groups are preferred.

The expression nonaromatic $C_3$–$C_{15}$ carbocyclic radical is understood to mean a condensed or bridged, saturated, mono- or polycyclic radical. These radicals comprise in particular the following radicals:

cyclopentyl, cyclohexyl, adamantyl, bicyclo[3.2.1]octyl, as well as 1,3,3-trimethylbicyclo[2.2.1]heptyl or fenchyl, 7,7-dimethylbicyclo[4.1.0]hep-3-yl.

The expression halogen is understood to mean a chlorine, bromine, fluorine or iodine atom.

The possible salts of the compounds of formula (I) comprise the pharmaceutically acceptable acid addition salts such as the hydrochloride, hydrobromide, sulfate, hydrogen sulfate, dihydrogen phosphate, methanesulfonate, methyl sulfate, maleate, oxalate, fumarate, naphthalenesulfonate, glyconate, gluconate, citrate, isethionate, para-toluenesulfonate, methylenesulfonate, benzenesulfonate or succinate.

The subject of the present invention is most particularly compounds of formula:

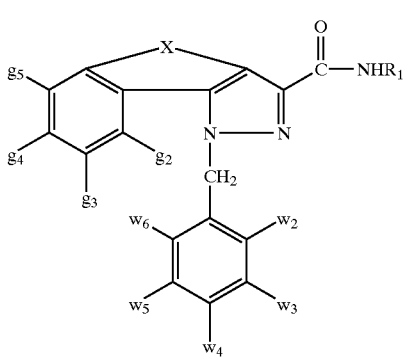

(I)

in which:
X— represents a group —(CH$_2$)$_n$—;
n is equal to 1 or 2;
g$_2$, g$_3$, g$_4$, g$_5$, w$_2$, w$_3$, w$_4$, w$_5$, w$_6$ are identical or different and each independently represent hydrogen, a halogen, a trifluoromethyl, a (C$_1$–C$_3$)alkyl, a (C$_1$–C$_3$)alkoxy, a (C$_1$–C$_3$)alkylthio, a nitro;
R$_1$ represents a nonaromatic C$_3$–C$_{15}$ carbocyclic radical which is unsubstituted or substituted one or several times with a (C$_1$–C$_4$)alkyl;
as well as their salts and their solvates.

Among the compounds of formula (I), those in which g$_2$, g$_5$, w$_5$, w$_6$ represent hydrogen and g$_3$, g$_4$, w$_2$, w$_3$ and w$_4$ have one of the values defined above for the compounds of formula (I) except hydrogen are preferred.

More particularly, the compounds of formula (I) are preferred in which w$_2$, w$_3$ and w$_4$ represent chlorine or a methyl and g$_3$ and g$_4$ represents chlorine, bromine or a methyl, the other substituents w and g being hydrogen.

The compounds of formula (I) are also preferred in which R$_1$ represents a carbocyclic radical chosen from: 1,3,3-trimethylbicyclo[2.2.1]hept-2-yl, bicyclo[3.2.1]oct-3-yl, 7,7-dimethylbicyclo[4.1.0]hept-3-yl.

Among the compounds of formula (I) those in which —X— represents a group —CH$_2$—CH$_2$—, and those in which —X— represents a group —CH$_2$— can be distinguished. The compounds of formula (I) in which —X— represents —CH$_2$— are preferred.

In the description, the following abbreviations are used:
ether: diethyl ether
iso ether: diisopropyl ether
EtOH: ethanol
MeOH: methanol
DCM: dichloromethane
AcOEt: ethyl acetate
LiHMDS: lithium salt of hexamethyldisilazane
(CO$_2$Et)$_2$: ethyl oxalate
PTSA: para-toluenesulfonic acid
PPA: polyphosphoric acid
DIBAL: diisobutylaluminum hydride
AcOH: acetic acid
RT: room temperature
m.p.: melting point
b.p.: boiling point
p: pressure
NMR: nuclear magnetic resonance. The NMR spectra are recorded at 200 MHz in DMSO d6
s: singlet; d: doublet; t: triplet; m: unresolved complex or multiplex.

The subject of the present invention is also a method for preparing a compound according to the invention, its salts and its solvates. This method is characterized in that a functional derivative of an acid of formula:

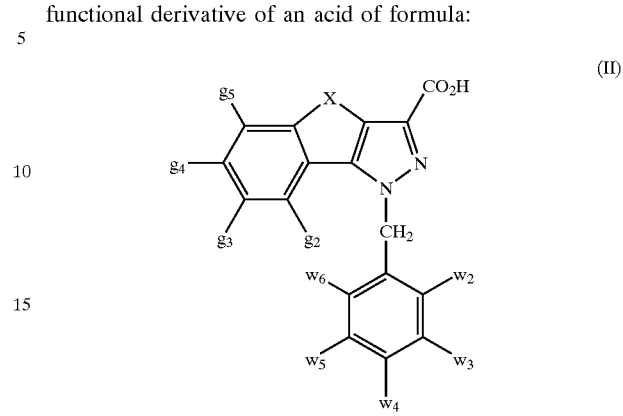

(II)

in which —X— and g$_2$, g$_3$, g$_4$, g$_5$, w$_2$, w$_3$, w$_4$, w$_5$, w$_6$ are as defined above for (I), is treated with a compound of formula NH$_2$R$_1$ (III), in which R$_1$ is as defined above for (I).

The reaction is carried out in a basic medium, for example in the presence of triethylamine in a solvent such as dichloromethane or tetrahydrofuran.

As a functional derivative of the acid (II), it is possible to use the acid chloride, the anhydride, a mixed anhydride, a C$_1$–C$_4$ alkyl ester in which the alkyl is straight or branched, an activated ester, for example the p-nitrophenyl ester, or the free acid which is opportunely activated, for example, with N,N-dicyclohexylcarbodiimide or with benzotriazol-N-oxotris(dimethylamino)phosphonium hexafluorophosphate (BOP).

Thus, by the method according to the invention, it is possible to react the acid chloride of formula (II) obtained by reacting thionyl chloride with the acid of formula (II) in an inert solvent such as benzene or toluene or a chlorinated solvent (dichloromethane, dichloroethane, chloroform for example), an ether (tetrahydrofuran, dioxane for example) or an amide (N,N-dimethylformamide for example) under an inert atmosphere, at a temperature of between 0° C. and the reflux temperature of the solvent.

A variant to the procedure consists in preparing the mixed anhydride of the acid of formula (II) by reacting ethyl chloroformate with the acid of formula (II), in the presence of a base such as triethylamine.

The starting acid (II) is novel and constitutes another aspect of the present invention, its functional derivatives are also novel, in particular its acid chloride and its C$_1$–C$_4$ alkyl ester.

The acid of formula (II) may be obtained according to the reaction scheme below:

SCHEME 1

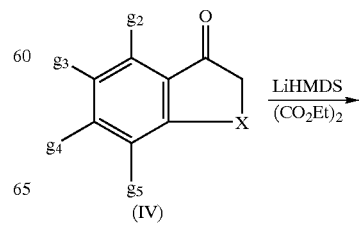

(IV)

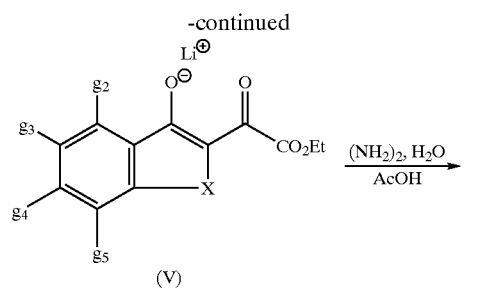

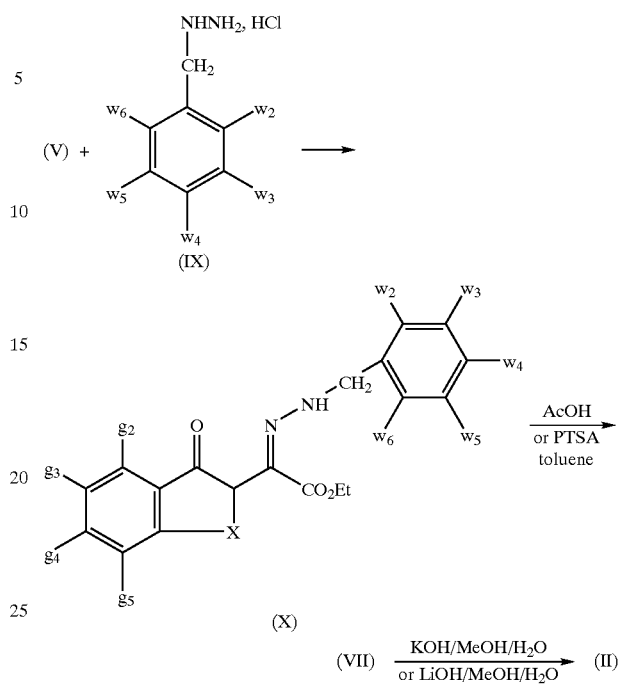

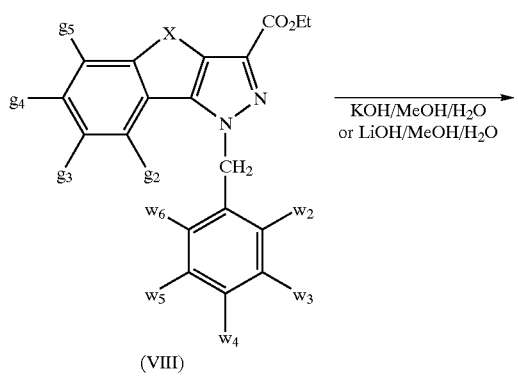

Using the method according to SCHEME 1, by the action of the benzyl halide derivative of formula (VII) on the compound of formula (VI), there may also be formed a position isomer of the compound of formula (VIII), namely a compound of formula

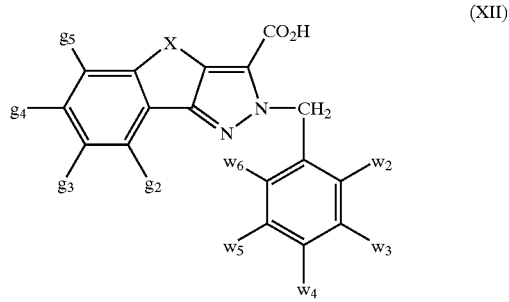

Likewise, using the method according to SCHEME 2, by the action of the benzylhydrazine derivative of formula (IX) in which $w_2$ to $w_6$ are as defined above for (I), there may also be formed a position isomer of the compound of formula (VIII), namely a compound of formula (XI).

To obtain the acid of formula (II), it is possible to either separate the 2 isomers of formula (VIII) and (XI), or to carry out the hydrolysis of the mixture of the isomers (VIII) and (XI) in order to prepare a mixture of the acid of formula (II) and of its isomer of formula:

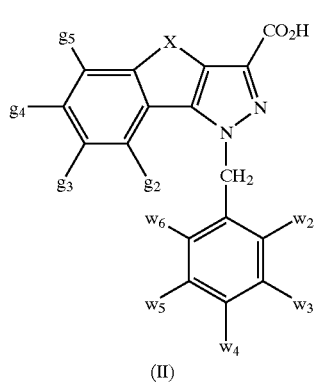

The acid of formula (II) may also be prepared by the action of a derivative of the benzylhydrazine of formula (IX) on a compound of formula (V), according to SCHEME 2 below.

The separation of the isomers is carried out by conventional methods, for example by chromatography or by crystallization.

The compounds of formula (IV) are known or prepared by known methods. For example, the tetralones of formula (IV) in which —X— represents —CH$_2$—CH$_2$— are known or prepared by known methods as described in Synthetic Communications, 1991, 21, 981–987.

The lithium salt of formula (V) is prepared by the action of the lithium salt of hexamethyldisilazane and then of ethyl oxalate.

By the action of hydrazine hydrate, and then heating in the presence of acetic acid or in the presence of para-toluenesulfonic acid in toluene, the compound of formula (VI) is prepared. The compound of formula (VI) is then treated with a strong base such as sodium hydride or sodium amide in a solvent and then a benzyl halide of formula (VII) in which Hal represents a halogen, preferably chlorine or bromine, and w$_2$-w$_6$ are as defined above for (I) is caused to act. A saponification is then carried out according to conventional methods, for example in the presence of potassium hydroxide or lithium hydroxide in methanol, in order to obtain the expected acid of formula (II).

The benzyl halides of formula (VII) are known or prepared by known methods.

In general, the compounds of formula (VII) in which Hal represents a bromine atom may be prepared by the action of N-bromosuccinimide on the corresponding derivatives of methylbenzene in the presence of dibenzoyl peroxide. It is also possible to prepare a benzyl bromide from a corresponding benzyl alcohol by the action of hydrobromic acid in solution in water or in acetic acid. It is also possible to use the action of phosphorus tribromide on a corresponding benzyl alcohol in order to prepare a compound of formula (VII) in which Hal represents a bromine atom.

The compounds of formula (VII) in which Hal represents an iodine atom may be prepared by the action of sodium iodide on a compound of formula (VII) in which Hal represents a chlorine atom in a solvent such as acetone or butan-2-one.

The compounds of formula (VII) in which Hal represents a chlorine atom may be prepared by the action of thionyl chloride on a corresponding benzyl alcohol.

The starting amine-containing derivatives of formula (III) are known or prepared by known methods, in particular those described in EP-A-868 420. (1S)-endo-1,3,3-trimethylbicyclo[2.2.1]heptan-2-ylamine is prepared according to J. Am. Chem. Soc., 1951, 73, 3360 or according to J. Med. Chem., 1991, 34, 1003–1010. Bicyclo[3.2.1] octan-3-ylamine is prepared according to H. Maskill et al., J. Chem. Soc. Perkin Trans II, 1984, 1369.

The compound of formula (I) obtained by the method according to the invention is isolated in the form of a free base or salt or solvate, according to conventional techniques.

The compound of formula (I) may be isolated in the form of one of its salts, for example the hydrochloride or oxalate; in this case, the free base may be prepared by neutralizing said salt with an inorganic or organic base, such as sodium or ammonium hydroxide, triethylamine or an alkali metal carbonate or bicarbonate such as sodium or potassium carbonate or bicarbonate, and converted to another salt such as methanesulfonate, fumarate or 2-naphthalenesulfonate.

When the compound of formula (I) is obtained in the form of a free base, the salification is carried out by treating with the chosen acid in an organic solvent. By treating the free base, dissolved for example in an ether such as diethyl ether or in acetone, with a solution of the acid in the same solvent, the corresponding salt is obtained which is isolated according to conventional techniques.

The compounds of formula (I) possess a very good affinity in vitro for the cannabinoid CB$_2$ receptors, under the experimental conditions described by Devane et al., Mol. Pharmacol., 1988, 34, 605–613.

More particularly, the compounds of the present invention, as they are or in the form of one of their pharmaceutically acceptable salts, are potent and selective antagonists of the cannabinoid CB$_2$ receptors, having a Ki of less than 5×10$^{-7}$ M. They are at least 10 times more active on the CB$_2$ receptors than on the CB$_1$ receptors and are active by the oral route.

Moreover, their antagonist nature has been demonstrated by the results in the models for inhibition of adenylate-cyclase induced by forskolin as described in M. Rinaldi-Carmona et al., J. Pharm. Exp. Therap., 1998, 284, 644–650.

The toxicity of the compounds (I) is compatible with their use as a medicament.

According to another of its aspects, the present invention relates to the use of the compounds of formula (I), or of one of their pharmaceutically acceptable salts and solvates, for the preparation of medicaments intended for treating diseases involving the cannabinoid CB$_2$ receptors.

The diseases for the treatment of which the compounds (I) and, optionally, their pharmaceutically acceptable salts may be used are pathologies involving the cells of the immune system or immune disorders, for example AIDS, autoimmune diseases, diseases related to organ transplants, infectious diseases, allergic diseases, diseases of the gastrointestinal system, for example Crohn's disease, inflammatory bowel disease; more particularly there may be mentioned the following autoimmune diseases: systemic lupus erythematosis, diseases of the connective tissue or collagen disease, Sjögren's syndrome, ankylosing spondylitis, reactive arthritis, rheumatoid arthritis, undifferentiated spondylarthritis, Behcet's disease, autoimmune hemolytic anemia, multiple sclerosis, psoriasis. The allergic diseases to be treated may be of the immediate or delayed hypersensitivity type, asthma for example. Likewise, the compounds and their possible pharmaceutically acceptable salts may be used for treating vasculitis, parasitic infections, viral infections, bacterial infections, amylosis, diseases affecting the lines of the lymphohematopoietic system.

The compounds according to the invention are also useful as anti-inflammatory agent, as anti-arthritic agent, as analgesic, in the treatment and prevention of vertigo, emesis and nausea, in particular nausea induced by anticancer agents, in the treatment of diabetes and in the treatment of ocular diseases, for example ocular hypertension or glaucoma.

Furthermore, the compounds according to the invention may be useful in the treatment of certain diseases of the central or peripheral nervous system, for example epilepsy, psychotic disorders, Alzheimer's disease, Parkinson's disease, Tourette's disease, Huntington chorea, as well as in the treatment of certain cancers.

Thus, according to another of its aspects, the present invention relates to a method for treating the above diseases which consists in administering to a patient requiring it an effective quantity of a compound of formula (I) or of one of its pharmaceutically acceptable salts.

The compounds (I) according to the invention, as they are or in radio-labeled form may moreover be used as pharmacological tools in humans or in animals, for the detection and labeling of peripheral cannabinoid CB$_2$ receptors. That constitutes a subsequent aspect of the present invention.

The compounds according to the invention are generally administered as a dosage unit.

Said dosage units are preferably formulated in pharmaceutical compositions in which the active ingredient is mixed with a pharmaceutical excipient.

Thus, according to another of its aspects, the present invention relates to pharmaceutical compositions containing, as active ingredient, a compound of formula (I), one of its pharmaceutically acceptable salts or one of their solvates. The above compounds of formula (I) and their pharmaceutically acceptable salts or solvates may be used at daily doses of 0.01 to 100 mg per kg of body weight of the mammal to be treated, preferably at daily doses of 0.1 to 50 mg/kg. In human beings, the dose may preferably vary from 0.5 to 4 000 mg per day, more particularly from 2 to 1 000 mg per day according to the age of the subject to be treated or the type of treatment, namely prophylactic or curative. Although these doses are examples of average situations, there may be specific cases where higher or lower doses are appropriate, such doses also belong to the invention. According to the usual practice, the dosage appropriate for each patient is determined by the doctor according to the mode of administration, the weight and the response of said patient.

In the pharmaceutical compositions of the present invention for oral, sublingual, inhaled, subcutaneous, intramuscular, intravenous, transdermal, local or rectal administration, the active ingredient may be administered in unit form for administration, as a mixture with conventional pharmaceutical carriers, to animals and to human beings. The appropriate unit forms for administration comprise the forms for administration by the oral route such as tablets, gelatin capsules, powders, granules and oral solutions or suspensions, the forms for sublingual and buccal administration, aerosols, the forms for topical administration, implants, the forms for subcutaneous, intramuscular, intravenous, intranasal or intraocular administration and the forms for rectal administration.

In the pharmaceutical compositions of the present invention, the active ingredient is generally formulated in the form of dosage units containing from 0.1 to 1 000 mg, advantageously from 0.5 to 500 mg, preferably from 1 to 200 mg of said active ingredient per dosage unit for daily administrations.

When a solid composition in tablet form is prepared, it is possible to add to the micronized or nonmicronized active ingredient a wetting agent such as sodium lauryl sulfate and the whole is mixed with a pharmaceutical vehicle such as silica, gelatin, starch, lactose, magnesium stearate, talc, gum arabic or the like. It is possible to coat the tablets with sucrose, with various polymers or with other appropriate materials or alternatively to treat them such that they have a prolonged or delayed activity and they continuously release a predetermined quantity of active ingredient.

A preparation in the form of gelatin capsules is obtained by mixing the active ingredient with a diluent such as a glycol or a glycerol ester and by incorporating the mixture obtained into soft or hard gelatin capsules.

A preparation in syrup or elixir form may contain the active ingredient together with a sweetener, preferably a calorie-free sweetener, methylparaben and propylparaben as antiseptics, as well as a flavoring agent and an appropriate colorant.

The water-dispersible powders or granules may contain the active ingredient as a mixture with dispersing agents, wetting agents or suspending agents, such as polyvinylpyrrolidone, as well as with sweeteners or flavor correctors.

For rectal administration, suppositories are used which are prepared with binders melting at the rectal temperature, for example cocoa butter or polyethylene glycols.

For parenteral, intranasal or intraocular administration, aqueous suspensions, isotonic saline solutions or sterile and injectible solutions which contain pharmacologically compatible dispersing agents and/or solubilizing agents, for example propylene glycol or polyethylene glycol, are used.

Thus, to prepare an aqueous solution which is injectible by the intravenous route, it is possible to use a cosolvent such as, for example, an alcohol such as ethanol or a glycol such as polyethylene glycol or propylene glycol, and a hydrophilic surfactant such as Tween® 80. To prepare an oily solution which is injectible by the intramuscular route, the active ingredient may be solubilized with a triglyceride or a glycerol ester.

For local administration, creams, ointments or gels may be used.

For transdermal administration, patches may be used in multilaminate form or in a form containing reservoirs in which the active ingredient may be in alcoholic solution.

For administration by inhalation, an aerosol is used containing, for example, sorbitan trioleate or oleic acid as well as trichlorofluoromethane, dichlorofluoromethane, dichlorotetrafluoroethane or any other biologically compatible propellant gas; it is also possible to use a system containing the active ingredient alone or combined with an excipient, in powdered form.

The active ingredient may be generally formulated in the form of microcapsules or microspheres, optionally with one or more carriers or additives.

The active ingredient may also be provided in the form of a complex with a cyclodextrin, for example α-, β- or γ-cyclodextrin, 2-hydroxypropyl-β-cyclodextrin or methyl-β-cyclodextrin.

Among the prolonged release forms which are useful in the case of chronic treatments, implants may be used. These may be prepared in the form of an oily suspension or in the form of a suspensions of microspheres in an isotonic medium.

PREPARATIONS

Preparation 1.1

Ethyl ester of 6-chloro-1,4-dihydroindeno[1,2-c] pyrazole-3-carboxylic acid (VI): $X=CH_2$, $g_4=Cl$ A) Ethyl ester of the lithium salt of (5-chloro-1-oxidoindan-2-yl)oxoacetic acid A solution of 4.42 g of LiHMDS is prepared at −60° C. in 140 ml of $Et_2O$ and a solution of 4.0 g of 5-chloroindan-1-one in 10 ml of $Et_2O$ is added dropwise. The mixture is kept stirring for 30 minutes, while allowing the temperature to rise to −30° C. and then 3.6 ml of ethyl oxalate are added. After stirring for 18 hours at RT, the yellow precipitate obtained is filtered, washed with water and then dried under vacuum. 6.42 g of the expected compound are obtained.

B) Ethyl ester of 6-chloro-1,4-dihydroindeno[1,2-c]-pyrazole-3-carboxylic acid 0.56 ml of hydrazine hydrate is added to a solution, cooled on an ice bath, containing 3 g of the compound obtained in the preceding step in 20 ml of acetic acid. The mixture is heated under reflux for 18 hours and then the reaction mixture is poured into 100 ml of ice-cold water. The mixture is filtered, washed with water and then dried under vacuum to give 2.62 g of the expected compound, m.p.=190° C.

NMR: 1.25 ppm: t: 3H; 3.70 ppm: s: 2H; 4.25 ppm: q: 2H; 7.25–7.65 ppm: m: 3H; 13.80 ppm: s: 1H.

Preparation 1.2

Ethyl ester of 6-chloro-7-methyl-1,4-dihydroindeno[1,2-c]pyrazole-3-carboxylic acid (VI): $X=CH_2$, $g_3=CH_3$, $g_4=Cl$ A) 3-Chloro-1-(4-chloro-3-methylphenyl)propan-1-one 23.43 ml of 2-chlorotoluene and 26.6 g of 3-chloropropionyl chloride are mixed in 25 ml of carbon sulfide and 32 g of $AlCl_3$ in 125 ml of carbon sulfide are added over 45 minutes. After stirring for 3 hours at RT, the solvent is evaporated and then 1 liter of water is added. The reaction medium is extracted with ether and then with benzene, and then the organic phase is washed with a saturated $Na_2CO_3$ solution and then with water. It is dried over $Na_2SO_4$ and then the residue is chromatographed on a silica column, eluting with an AcOEt/cyclohexane (5/95; v/v) mixture. 27.25 g of the expected compound are obtained.

NMR: 2.4 ppm: s: 3H; 3.6 ppm: t: 2H; 3.9 ppm: t: 2H; 7.6 ppm: m: 1H; 7.8 ppm: m: 1H; 8 ppm: m: 1H.

B) 5-Chloro-6-methylindanone 250 ml of concentrated $H_2SO_4$ are slowly added, with vigorous stirring, to 30.67 g of the compound prepared in the preceding step. The mixture is heated at 90° C. for one hour and then poured over ice. The mixture is extracted with ether and then the organic phase is dried over $Na_2SO_4$ and evaporated to dryness. The residue is chromatographed on silica, eluting with an AcOEt/cyclohexane (5/95; v/v) mixture. 1.8 g of the expected compound are obtained.

NMR: 2.3 ppm: s: 3H; 2.5–2.6 ppm: m: 2H; 2.9–3 ppm: m: 2H; 7.5 ppm: s: 1H; 7.6 ppm: s: 1H.

C) Ethyl ester of 6-chloro-7-methyl-1,4-dihydroindeno[1,2-c]pyrazole-3-carboxylic acid The procedure is then carried out as described in PREPARATION 1.1 in steps A and B in order to prepare the expected compound.

NMR: 1.2 ppm: t: 3H; 2.3 ppm: s: 3H; 3.6 ppm: s: 2H; 4.2 ppm: q: 2H; 7.4 ppm: s: 1H; 7.5 ppm: s: 1H; 13.7 ppm: s: 1H.

By carrying out the procedure according to PREPARATION 1.1, the compounds described in TABLE 1 are prepared.

TABLE 1

(VI)

| Preparation | X | $g_2$ | $g_3$ | $g_4$ | $g_5$ | m.p. °C. |
|---|---|---|---|---|---|---|
| 1.3 | $CH_2$ | H | H | Br | H | NMR: 1.4 ppm: t: 3H; 3.8 ppm: s: 2H; 4.4 ppm: q: 2H; 7.6–7.8 ppm: m: 2H; 7.9 ppm: s: 1H; 13.9 ppm: s: 1H |
| 1.4 | $CH_2$—$CH_2$ | H | H | Cl | H | 170° C. |

Preparation 2.1

1-(2,4-Dichlorobenzyl)-6-chloro-1,4-dihydroindeno[1,2-c]pyrazole-3-carboxylic acid II, $X=CH_2$; $g_4=w_2=w_4=Cl$ A) Ethyl ester of 1-(2,4-dichlorobenzyl)-6-chloro-1,4-dihydroindeno[1,2-c]pyrazole-3-carboxylic acid A suspension of 2.48 g of the compound obtained in PREPARATION 1 is prepared in 50 ml of toluene and 0.45 g of 60% sodium hydride in oil is added in 3 portions, and then the mixture is heated at 65° C. for 1 hour. After returning to RT, 1.38 ml of 2,4-dichlorobenzyl chloride are added and then the mixture is heated under reflux for 44 hours. 100 ml of a saturated $NH_4Cl$ solution is added, the medium is filtered and then the organic phase is evaporated under vacuum and the residue is mixed with the precipitate and triturated in AcOEt. The mixture is filtered, washed with AcOEt and then dried under vacuum to give 3.00 g of the expected compound, m.p.=168° C.

B) 1-(2,4-Dichlorobenzyl)-6-chloro-1,4-dihydroindeno[1,2-c]pyrazole-3-carboxylic acid 2.97 g of the compound obtained in the preceding step are placed in 60 ml of MeOH, 1.01 g of KOH in 10 ml of water are added and then the mixture is heated under reflux for 4 hours. The reaction medium is then poured into a mixture containing 200 ml of ice-cold water and 20 ml of 10% HCl. The mixture is filtered, washed with water and then dried under vacuum to give 2.50 g of the expected compound, m.p.>260° C.

NMR: 3.75 ppm: s: 2H; 5.80 ppm: s: 2H; 7.05 ppm: d: 1H; 7.30–7.80 ppm: m: 5H.

By carrying out the procedure according to PREPARATION 2.1, the compounds described in the TABLE below are prepared.

TABLE 2

(II)

| Preparation | X | $g_3$ | $g_4$ | $w_2$ | $w_3$ | $w_4$ | NMR/m.p. °C. |
|---|---|---|---|---|---|---|---|
| 2.2 | —$CH_2$— | H | Cl | H | Cl | $CH_3$ | 2.2 ppm: s: 3H; 3.8 ppm: s: 2H; 5.7 ppm: s: 2H; 7–7.8 ppm: m: 6H; 12.4–13 ppm: m: 1H |
| 2.3 | $CH_2$ | H | Br | H | H | $CH_3$ | 2.2 ppm: s: 3H; 3.6 ppm: s: 2H; 5.5 ppm: s: 2H; 7 ppm: s: 4H; 7.4 ppm: |

TABLE 2-continued (II)

[Structure of compound II showing benzofused pyrazole with CO2H group, X linker, substituents g2-g5 on aromatic ring, CH2 linker to benzyl with substituents w2-w6]

| Preparation | X | g3 | g4 | w2 | w3 | w4 | NMR/m.p. ° C. |
|---|---|---|---|---|---|---|---|
| 2.4 | CH2 | H | Br | H | Cl | Cl | s: 2H; 7.7 ppm: s: 1H 3.7 ppm: s: 2H; 5.7 ppm: s: 2H 7.2–7.3 ppm: dd: 1H; 7.5–7.7 ppm: m: 4H; 7.8 ppm: s: 1H |
| 2.5 | CH2 | H | Br | Cl | H | Cl | 3.7 ppm: s: 2H; 4–5 ppm: m: 1H; 5.6 ppm: s: 2H; 6.9 ppm: d: 1H; 7.2–7.4 ppm: dd: 1H; 7.7 ppm: s: 1H; 7.8 ppm: s: 1H |
| 2.6 | CH2 | CH3 | Cl | H | Cl | Cl | 2.4 ppm: s: 3H; 3.6 ppm: s: 2H; 4.2–4.4 ppm: m: 1H; 5.8 ppm: s: 2H; 7.3 ppm: d: 1H; 7.7 ppm: t: 1H; 7.9 ppm: d: 1H |
| 2.7 | CH2—CH2 | H | Cl | Cl | H | Cl | 2.90 ppm: s: 2H; 5.70 ppm: s: 2H; 6.65 ppm: d: 1H; 7.20–7.70 ppm: m: 4H |
| 2.8 | CH2 | H | Br | H | H | Cl | 276° C. |
| 2.9 | CH2 | H | Br | H | H | CF3 | 263° C. |
| 2.10 | CH2—CH2 | H | OMe | H | Cl | Cl | 221° C. |

Preparation 3

7,7-Dimethylbicyclo[4.1.0]hept-3-ylamine, hydrochloride

A) 7,7-Dimethylbicyclo[4.1.0]heptan-3-one oxime 5 g of 7,7-dimethylbicyclo[4.1.0]hept-3-one are dissolved in 25 ml of MeOH and 18 ml of CHCl3 and 3.77 g of hydroxylamine and 5.9 g of sodium acetate dissolved in 100 ml of water are added. The mixture is heated under reflux for 56 hours and then cooled. It is extracted with ether and then the ethereal phase is dried over Na2SO4 and evaporated to dryness. The oil obtained (6.56 g) is used as it is in the next step.

B) 7,7-Dimethylbicyclo[4.1.0]hept-3-ylamine, hydrochloride 6.5 g of the product obtained in the preceding step is dissolved in 150 ml of EtOH and the mixture is placed in a hydrogen bomb. 3 ml of CHCL3 and 1.5 g of PtO2 are added and then the mixture is left under an H2 atmosphere at a pressure of 7.8 bar for 72 hours. The mixture is filtered on Celite®, evaporated to dryness, and then taken up in ether, drained and dried under vacuum. 3.37 g of the expected compound are obtained.

NMR: 0.95 ppm: s: 3H; 1.10 ppm: s: 3H; 1.50–2.30 ppm: m: 8H; 3.40–3.55 ppm: m: 1H; 8.00 ppm: s: 2H.

EXAMPLE 1

N-[(1S)-1,3,3-Trimethylbicyclo[2.2.1]hept-2-endo-yl-6-chloro-1-(2,4-dichlorobenzyl)-1,4-dihydroindeno[1,2-c]-pyrazole-3-carboxamide I, X=CH2; g4=w2=w4=Cl;

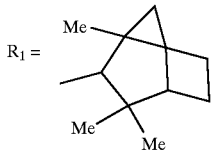

A) 1-(2,4-dichlorobenzyl)-6-chloro-1,4-dihydroindeno[1,2-c]pyrazole-3-carboxylic acid chloride 2.45 g of the compound obtained in PREPARATION 2.1 in 35 ml of toluene and 1.36 ml of SOCl2 are mixed and the mixture is heated under reflux for 2 hours. The solvent is evaporated under vacuum and then the residue is taken up in 30 ml of toluene and evaporated to dryness (twice). 2.59 g of the expected compound are obtained.

B) N-[(1S)-1,3,3-Trimethylbicyclo[2.2.1]hept-2-endo-yl-6-chloro-1-(2,4-dichlorobenzyl)-1,4-dihydro-indeno[1,2-c]pyrazole-3-carboxamide A solution of 0.80 g of the compound obtained in the preceding step in 20 ml of DCM is added dropwise over a solution, cooled to 0° C., of 0.37 g of (1S)-endo-1,3,3-trimethylbicyclo[2.2.1]hept-2-ylamine and 0.55 ml of NEt3 in 20 ml of DCM. The mixture is kept stirring at RT for 16 hours and then the reaction medium is poured over 100 ml of ice-cold water. The mixture is extracted with DCM, the solvent is evaporated, dried over MgSO4 and then the residue is chromatographed on silica, eluting with an AcOEt/toluene (1/9; v/v) mixture. The compound obtained crystallizes from isopropyl ether. 0.46 g is obtained, m.p.= 157° C.

NMR: 0.75 ppm: s: 3H; 1.00–1.75 ppm: m: 13H; 3.65 ppm: d: 1H; 3.80 ppm: s: 2H; 5.80 ppm: s: 2H; 6.90–7.10 ppm: m: 2H; 7.35–7.45 ppm: m: 2H; 7.55–7.70 ppm: m: 3H.

By carrying out the procedure according to EXAMPLE 1, the compounds according to the invention described in the TABLE below are prepared, TABLE 3
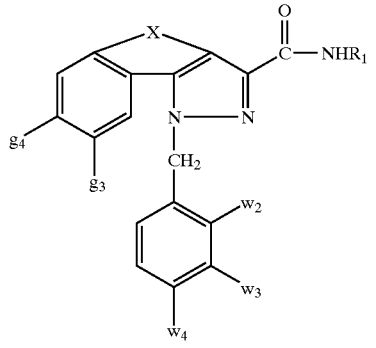
(I)
| Examples | X | g₃ | g₄ | w₂ | w₃ | w₄ | R₁ | α_D | m.p. |
|---|---|---|---|---|---|---|---|---|---|
| 2 | CH₂ | H | Cl | Cl | H | Cl | 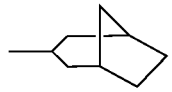<br>endo | | 197 |
| 3 | CH₂ | H | Cl | H | Cl | Cl | 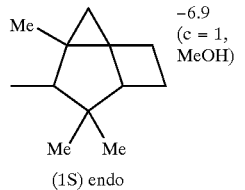<br>(1S) endo | −6.9<br>(c = 1,<br>MeOH) | 158 |
| 4 | CH₂ | H | Cl | H | Cl | Cl | 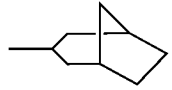<br>endo | | 93 |
| 5 | CH₂ | H | Cl | H | Cl | CH₃ | 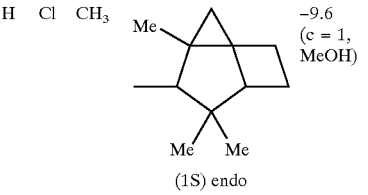<br>(1S) endo | −9.6<br>(c = 1,<br>MeOH) | 78–83 |
| 6 | CH₂ | H | Cl | H | Cl | CH₃ | 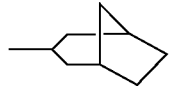<br>endo | | 74–78 |
| 7 | CH₂ | H | Br | H | H | CH₃ | 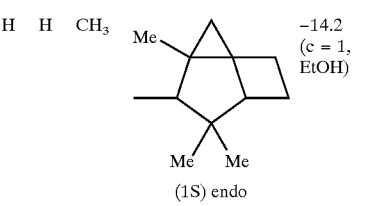<br>(1S) endo | −14.2<br>(c = 1,<br>EtOH) | 78 |

TABLE 3-continued (I)

| Examples | X | g₃ | g₄ | w₂ | w₃ | w₄ | R₁ | α_D | m.p. |
|---|---|---|---|---|---|---|---|---|---|
| 8 | CH₂ | H | Br | H | H | CH₃ | (cyclohexyl with gem-dimethyl) R (+) | −18.3 (c = 1, EtOH) | 105 |
| 9 | CH₂ | H | Br | H | Cl | Cl | (norbornyl, Me, Me, Me) (1S) endo | −10.3 (c = 1, EtOH) | 149 |
| 10 | CH₂ | H | Br | Cl | H | Cl | (norbornyl, Me, Me, Me) (1S) endo | −7.2 (c = 1, EtOH) | 92 |
| 11 | CH₂ | CH₃ | Cl | H | Cl | Cl | (norbornyl, Me, Me, Me) (1S) endo | −7.3 (c = 1, EtOH) | 100 |
| 12 | CH₂ | CH₃ | Cl | H | Cl | Cl | (norbornyl, Me) endo | | 90 |
| 13 | CH₂—CH₂ | H | Cl | Cl | H | Cl | (norbornyl, Me, Me, Me) (1S) endo | −1.2 (c = 1, EtOH) | 97 |

TABLE 3-continued (I)

| Examples | X | g₃ | g₄ | w₂ | w₃ | w₄ | R₁ | α_D | m.p. |
|---|---|---|---|---|---|---|---|---|---|
| 14 | CH₂—CH₂ | H | OMe | H | Cl | Cl | endo | | 172 |
| 15 | CH₂—CH₂ | H | OMe | H | Cl | Cl | (1S) endo | −8.1 (c = 1; CHCl₃) | 104 |
| 16 | CH₂ | H | Br | Cl | H | Cl | endo | | 190 |
| 17 | CH₂ | H | Br | Cl | H | Cl | exo | | 196 |
| 18 | CH₂ | H | Br | H | H | Cl | (1S) endo | −8.8 (c = 1, MeOH) | 82 |
| 19 | CH₂ | H | Br | H | H | Cl | endo | | 181 |
| 20 | CH₂ | H | Br | H | H | CF₃ | (1S) endo | −5.9 (c = 1, MeOH) | 85 |

TABLE 3-continued

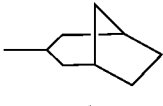

| Examples | X | $g_3$ | $g_4$ | $w_2$ | $w_3$ | $w_4$ | $R_1$ | $\alpha_D$ | m.p. |
|---|---|---|---|---|---|---|---|---|---|
| 21 | $CH_2$ | H | Br | H | H | $CF_3$ | endo | | 87 |

What is claimed is:

1. A compound of formula:

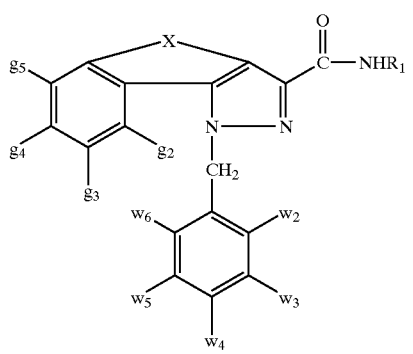

in which:

X— represents a group —$(CH_2)_n$—;
n is equal to 1 or 2;

$g_2$, $g_3$, $g_4$, $g_5$, $w_2$, $w_3$, $w_4$, $w_5$, $w_6$ are identical or different and each independently represent hydrogen, a halogen, a trifluoromethyl, a ($C_1$–$C_4$)alkyl, a ($C_1$–$C_4$)alkoxy, a ($C_1$–$C_4$)alkylthio, a nitro;

$R_1$ represents a nonaromatic $C_3$–$C_{15}$ carbocyclic radical which is unsubstituted or substituted one or several times with a ($C_1$–$C_4$)alkyl;

or a pharmaceutically acceptable salt or solvate thereof.

2. The compound as claimed in claim 1, in which $g_2$, $g_5$, $w_5$, $w_6$ represent hydrogen.

3. The compound as claimed in claim 2, in which $w_2$, $w_3$ and $w_4$ represent chlorine or a methyl and $g_3$ and $g_4$ represents chlorine, bromine or a methyl.

4. The compound as claimed in claim 3 of formula (I), in which $R_1$ represents a carbocyclic radical chosen from: 1,3,3-trimethylbicyclo[2.2.1]hept-2-yl, bicyclo[3.2.1]oct-3-yl, 7,7-dimethylbicyclo[4.1.0]hept-3-yl.

5. The compound as claimed in claim 1 of formula (I), in which —X— represents —$CH_2$—.

6. A method for preparing a compound as claimed in claim 1 wherein a functional derivative of an acid of formula:

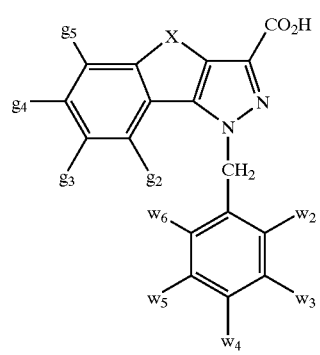

in which —X— and $g_2$, $g_3$, $g_4$, $g_5$, $w_2$, $w_3$, $w_4$, $w_5$, $w_6$ are as defined in claim 1 for (I), is treated with a compound of formula $NH_2R_1$ (III), in which $R_1$ is as defined in claim 1.

7. A pharmaceutical composition containing a compound as claimed in claim 1.

8. The pharmaceutical composition as claimed in claim 7, in dosage unit form.

9. The compound as claimed in claim 4 in which —X— represents —$CH_2$—.

10. A pharmaceutical composition containing a compound as claimed in claim 2.

11. A pharmaceutical composition containing a compound as claimed in claim 3.

12. A pharmaceutical composition containing a compound as claimed in claim 4.

13. A pharmaceutical composition containing a compound as claimed in claim 5.

14. A pharmaceutical composition containing a compound as claimed in claim 9.

* * * * *